United States Patent
Paolocci et al.

(10) Patent No.: US 10,786,543 B2
(45) Date of Patent: Sep. 29, 2020

(54) P75$^{NTR}$ ANTAGONISTS AND TREATMENT OF ACUTE AND CHRONIC CARDIAC DISEASE

(71) Applicant: THE JOHNS HOPKINS UNIVERSITY, Baltimore, MD (US)

(72) Inventors: Nazareno Paolocci, Baltimore, MD (US); Ning Feng, Baltimore, MD (US); Carlo G. Tocchetti, Baltimore, MD (US); Cyrus Takahashi, Baltimore, MD (US); Bruce Carter, Nashville, TN (US)

(73) Assignees: The Johns Hopkins University, Baltimore, MD (US); Vanderbilt University, Nashville, TN (US)

( * ) Notice: Subject to any disclaimer, the term of this patent is extended or adjusted under 35 U.S.C. 154(b) by 0 days.

(21) Appl. No.: 15/762,238

(22) PCT Filed: Sep. 22, 2016

(86) PCT No.: PCT/US2016/053001
§ 371 (c)(1),
(2) Date: Mar. 22, 2018

(87) PCT Pub. No.: WO2017/053506
PCT Pub. Date: Mar. 30, 2017

(65) Prior Publication Data
US 2018/0271931 A1 Sep. 27, 2018

Related U.S. Application Data

(60) Provisional application No. 62/221,749, filed on Sep. 22, 2015.

(51) Int. Cl.
*A61K 38/08* (2019.01)
*A61K 38/10* (2006.01)
*A61K 45/06* (2006.01)
*G01N 33/50* (2006.01)
*C07K 7/06* (2006.01)
*C07K 7/08* (2006.01)
*C07K 14/475* (2006.01)
*A61P 9/00* (2006.01)
*A61K 38/12* (2006.01)
*A61K 49/00* (2006.01)

(52) U.S. Cl.
CPC ............ *A61K 38/08* (2013.01); *A61K 38/10* (2013.01); *A61K 38/12* (2013.01); *A61K 45/06* (2013.01); *A61K 49/0004* (2013.01); *A61P 9/00* (2018.01); *C07K 7/06* (2013.01); *C07K 7/08* (2013.01); *C07K 14/475* (2013.01); *G01N 33/502* (2013.01); *G01N 33/5061* (2013.01); *G01N 33/5082* (2013.01); *G01N 2800/325* (2013.01)

(58) Field of Classification Search
CPC .......... A61K 38/08; A61K 38/10; C07K 7/06; C07K 7/08
See application file for complete search history.

(56) References Cited

U.S. PATENT DOCUMENTS

| | | | |
|---|---|---|---|
| 7,919,471 B2 * | 4/2011 | Bartlett | C07K 14/70571 514/44 R |
| 2003/0077826 A1 * | 4/2003 | Edelman | A61K 39/0011 435/440 |
| 2007/0054848 A1 * | 3/2007 | Tohyama | A61K 38/10 514/44 R |

FOREIGN PATENT DOCUMENTS

| | | |
|---|---|---|
| EP | 2163248 B1 | 8/2012 |
| WO | 2003/065997 A2 | 8/2003 |

OTHER PUBLICATIONS

Vaughn et al. Hypertensive emergencies. The Lancet. Jul. 29, 2000, vol. 356, pp. 411-417. (Year: 2000).*
Yaar, M., et al., "p75NTR Antagonistic Cyclic Peptide Decreases the Size of B Amyloid-Induced Brain Inflammation" Cell Mol Neurobiol (2008) 28:1027-1031.
Lorentz, C., et al., "Heterogeneous ventricular sympathetic innervation, altered B-adrenergic receptor expression, and rhythm instability in mice lacking the p75 neurotrophin receptor" Am J Physiol Heart Circ Physiol 298: H1652-H1660, 2010.
Takimoto, et al., Oxidant stress from nitric oxide synthase-3 uncoupling stimulates cardiac pathologic remodeling from chronic pressure load. J Clin Invest May 2005;115(5):1221-31.
Kaludercic, et al., Monoamine oxidase A-mediated enhanced catabolism of norepinephrine contributes to adverse remodeling and pump failure in hearts with pressure overload. Circ Res. Jan. 8, 2010;106(1):193-202.
Kaludercic, et al., Monoamine oxidase B prompts mitochondrial and cardiac dysfunction in pressure overloaded hearts. Antioxid Redox Signal. Jan. 10, 2014;20(2):267-80.
Sivakumaran, et al., HNO enhances SERCA2a activity and cardiomyocyte function by promoting redox-dependent phospholamban oligomerization. Antioxid Redox Signal. Oct. 10, 2013;19(11):1185-97.
Tocchetti, et al., Nitroxyl improves cellular heart function by directly enhancing cardiac sarcoplasmic reticulum Ca2 + cycling. Circ Res. Jan. 5, 2007;100(1):96-104.

* cited by examiner

*Primary Examiner* — Jeffrey E. Russel
(74) *Attorney, Agent, or Firm* — John Hopkins Technology Ventures

(57) ABSTRACT

The present invention provides 75 kD transmembrane neurotrophin receptor (p75$^{NTR}$) antagonists and their use in prevention and treatment of loss of function, and adverse remodeling, in cardiac tissues subject to acute or chronic hemodynamic stress. Uses of the antagonists with or without additional cardiotropic agents for improving contractility and for treatment of congestive heart failure are also provided.

17 Claims, 7 Drawing Sheets
Specification includes a Sequence Listing.

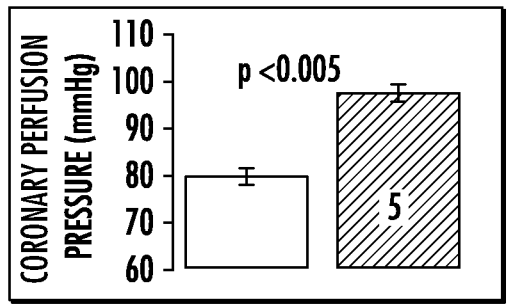
FIG. 4A
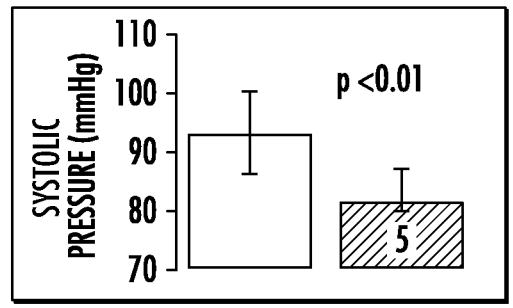
FIG. 4B
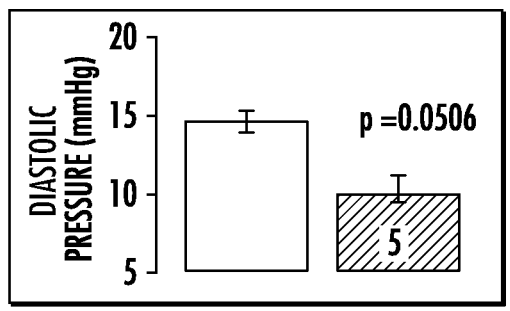
FIG. 4C
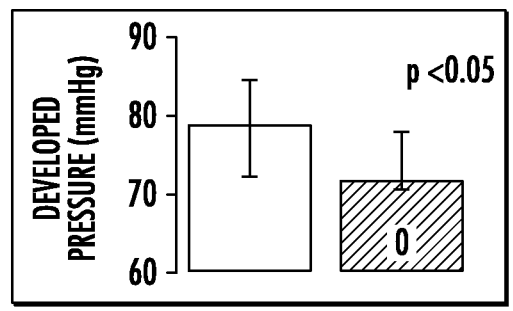
FIG. 4D
proBDNF     −     +
(1.5 nM × 20-30 min)
FIG. 4E
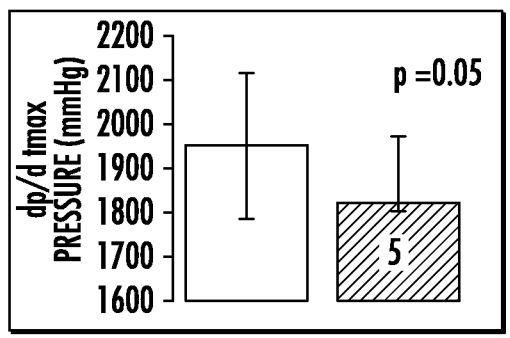
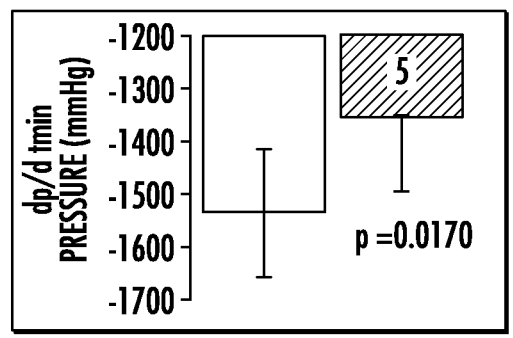
−     +
FIG. 4F

SEQUENCE LISTING

```
<160> NUMBER OF SEQ ID NOS: 9

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 1

Cys Ala Thr Asp Ile Lys Gly Ala Glu Cys
1               5                   10

<210> SEQ ID NO 2
<211> LENGTH: 8
<212> TYPE: PRT
<213> ORGANISM: Artificial Sequence
<220> FEATURE:
<223> OTHER INFORMATION: synthetic peptide sequence
```

```
<400> SEQUENCE: 2

Cys Ala Thr Asp Ile Lys Gly Ala
1               5

<210> SEQ ID NO 3
<211> LENGTH: 7
<212> TYPE: PRT
<213> ORGANISM: Artificial Sequence
<220> FEATURE:
<223> OTHER INFORMATION: synthetic peptide sequence

<400> SEQUENCE: 3

Cys Ala Thr Asp Ile Lys Gly
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic peptide sequence

<400> SEQUENCE: 4

Thr Asp Ile Lys Gly Ala Glu Cys
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic peptide sequence

<400> SEQUENCE: 5

Thr Asp Ile Lys Gly Ala Lys Glu Cys
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic peptide sequence

<400> SEQUENCE: 6

Thr Asp Ile Lys Gly Ala Glu
1               5

<210> SEQ ID NO 7
<211> LENGTH: 8
<212> TYPE: PRT
<213> ORGANISM: Artificial Sequence
<220> FEATURE:
<223> OTHER INFORMATION: synthetic peptide sequence

<400> SEQUENCE: 7

Ala Thr Asp Val Lys Gly Ala Glu
1               5

<210> SEQ ID NO 8
<211> LENGTH: 14
<212> TYPE: PRT
<213> ORGANISM: Artificial Sequence
<220> FEATURE:
<223> OTHER INFORMATION: synthetic peptide sequence
```

```
<400> SEQUENCE: 8

Ala Thr Leu Asp Ala Leu Leu Ala Ala Leu Arg Arg Ile Gln
1               5                   10

<210> SEQ ID NO 9
<211> LENGTH: 15
<212> TYPE: PRT
<213> ORGANISM: Artificial Sequence
<220> FEATURE:
<223> OTHER INFORMATION: synthetic peptide sequence

<400> SEQUENCE: 9

Cys Phe Phe Arg Gly Gly Phe Phe Asn His Asn Pro Arg Tyr Cys
1               5                   10                  15
```

P75$^{NTR}$ ANTAGONISTS AND TREATMENT OF ACUTE AND CHRONIC CARDIAC DISEASE

CROSS-REFERENCE TO RELATED APPLICATIONS

This application is a 35 U.S.C. § 371 U.S. national entry of International Application PCT/US2016/053001, having an international filing date of Sep. 22, 2016, which claims the benefit of U.S. Provisional Application No. 62/221,749, filed Sep. 22, 2015, the content of each of the aforementioned applications is herein incorporated by reference in their entirety.

STATEMENT OF GOVERNMENTAL INTEREST

This invention was made with government support under grant no. NS038220, awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Sep. 20, 2016, is named P13700-02_ST25.txt and is 2,072 bytes in size.

BACKGROUND OF THE INVENTION

The 75 kD transmembrane neurotrophin receptor (p75$^{NTR}$) (not to be confused with TNRF2) is a pleiotropic signaling molecule regulating neuronal survival, neurite outgrowth, and myelin formation. In neuronal cells, p75$^{NTR}$ is activated by uncleaved (immature) neurotrophins (proNTs), such as pro-nerve growth factor (proNGF) or pro-brain derived neurotrophic factor (proBDNF), or directly by oxidative stress. Regardless of the trigger, once activated, p75$^{NTR}$ engages sortilin, and this interaction in turn triggers a cell death pathway involving either Jun N-terminal kinase (JNK) or a ligand-dependent regulated intramembrane proteolysis (RIP) of p75$^{NTR}$. RIP promotes the release of the cytoplasmic tail of the receptor (ICD), which has signaling capacity allowing the nuclear translocation of the p75$^{NTR}$ adaptor NRIF (neurotrophin receptor interacting factor). The latter is an essential step of p75$^{NTR}$-induced cell death (FIG. 1).

SUMMARY OF THE INVENTION

In accordance with an embodiment, the present invention provides a pharmaceutical composition comprising a p75$^{NTR}$ antagonist and a pharmaceutically acceptable carrier. In some embodiments, the p75$^{NTR}$ antagonist is a peptide.

In accordance with an embodiment, the present invention provides a pharmaceutical composition comprising a p75$^{NTR}$ antagonist, wherein the p75$^{NTR}$ antagonist is a polypeptide comprising the following amino acid sequence a) CATDIKGAEC (SEQ ID NO: 1) or b) a functional fragment of a); c) a functional homolog of a) or b) or functional fragment thereof; and d) a fusion polypeptide comprising an amino acid sequence of any of a) to c).

In accordance with an embodiment, the present invention provides a method for improving contractility in cardiac tissue of a subject comprising administering to the subject an effective amount of a pharmaceutical composition comprising a p75$^{NTR}$ antagonist and a pharmaceutically acceptable carrier.

In accordance with an embodiment, the present invention provides a method for improving contractility in cardiac tissue of a subject comprising administering to the subject an effective amount of a pharmaceutical composition comprising a p75$^{NTR}$ antagonist, at least one additional cardiotropic agent, and a pharmaceutically acceptable carrier In accordance with an embodiment, the present invention provides a method for improving contractility in cardiac tissue of a subject comprising administering to the subject an effective amount of a pharmaceutical composition comprising a p75$^{NTR}$ antagonist comprising a polypeptide comprising the following amino acid sequence a) CATDIKGAEC (SEQ ID NO: 1) or b) a functional fragment of a); c) a functional homolog of a) or b) or functional fragment thereof; and d) a fusion polypeptide comprising an amino acid sequence of any of a) to c), and a pharmaceutically acceptable carrier.

In accordance with an embodiment, the present invention provides a method for treating congestive heart failure in a subject comprising administering to the subject an effective amount of a pharmaceutical composition comprising a p75$^{NTR}$ antagonist.

In accordance with an embodiment, the present invention provides a method for treating congestive heart failure in a subject comprising administering to the subject an effective amount of a pharmaceutical composition comprising a p75$^{NTR}$ antagonist, at least one additional cardiotropic agent, and a pharmaceutically acceptable carrier.

In accordance with an embodiment, the present invention provides methods for identifying target compounds having p75$^{NTR}$ antagonist activity comprising in vitro measurement of oxidative stress, cell death, contractility, relaxation and Ca$^{2+}$ transient currents in cardiac myocytes contacted with the target compounds or controls, and then contacting the cardiac myocytes with pro-BDNF, and identifying the target compounds as having p75$^{NTR}$ antagonist activity, when the amount of oxidative stress, cell death is decreased, and/or the amount of contractility, relaxation and Ca$^{2+}$ transient currents is increased, in cardiac myocytes contacted with the target compounds, relative to cardiac myocytes contacted with pro-BDNF without the target compounds.

In accordance with another embodiment, the present invention provides methods for identifying target compounds having p75$^{NTR}$ antagonist activity in a whole heart preparation in vitro comprising: a) contacting one or more whole heart preparations with a solution comprising a target molecule or a control solution; b) contacting the whole heart preparations of a) contacted with the solution comprising the target molecule, or contacted with the control solution with a solution comprising an effective amount of proBDNF; c) measuring coronary perfusion pressure and/or left-ventricle function and/or relaxation in the whole heart preparations of b); and d) identifying the target molecule as having p75$^{NTR}$ antagonist when the amount of contractility and/or relaxation is increased, or the amount of adverse cardiac remodeling is decreased, in the whole heart preparations of b) contacted with the solution comprising the target molecule relative to the isolated cardiac myocytes contacted with the control solution.

In some embodiments, the present invention provides a screening assay comprising a plurality of mice which have heart failure that was induced by transverse aortic constriction (TAC), simulating aortic stenosis that are treated with a compound of interest are compared to a plurality of mice which have heart failure that was induced by TAC that are treated with a control composition, wherein the TAC mice are used to measure in vivo pressure-volume relationships to determine load-independent indexes of myocardial contractility and in vivo remodeling, testing the impact of the above mentioned interventions on in vivo heart function and response to chronic stressing conditions.

BRIEF DESCRIPTION OF THE DRAWINGS

FIGS. 4A-4F depict the impact of proBDNF infusion on isolated normal mouse heart function.

DETAILED DESCRIPTION OF THE INVENTION

Figure 1:
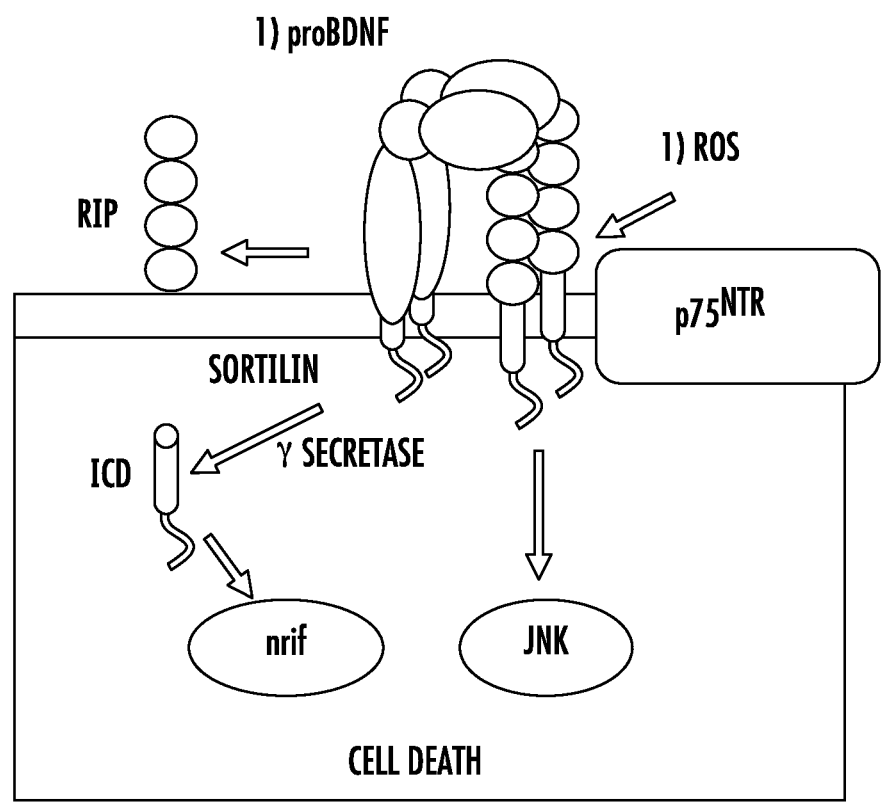
FIG. 1 illustrates the proposed mechanisms for $p75^{NTR}$ activation and associated downstream signaling cascade leading to myocardial apoptosis in chronically stressed hearts.

In accordance with one or more embodiments, the present invention provides $p75^{NTR}$ antagonists that can improve cardiac function under acute and chronic cardiac conditions via administration of an effective amount to a subject in need thereof.

In some embodiments, the selective $p75^{NTR}$ antagonists include the peptide CATDIKGAEC (SEQ ID NO: 1) or b) a functional fragment of a); c) a functional homolog of a) or b) or functional fragment thereof; and d) a fusion polypeptide comprising an amino acid sequence of any of a) to c).

Functional fragments of the selective $p75^{NTR}$ antagonists can include, for example, CATDIKGA (SEQ ID NO: 2), CATDIKG (SEQ ID NO: 3), TDIKGAEC (SEQ ID NO: 4), TDIKGAKEC (SEQ ID NO: 5), TDIKGAE (SEQ ID NO: 6), and ATDVKGAE (SEQ ID NO: 7).

In an alternative embodiment, the selective $p75^{NTR}$ antagonists include the peptide ATLDALLAALRRIQ (SEQ ID NO: 8) or b) a functional fragment of a); c) a functional homolog of a) or b) or functional fragment thereof; and d) a fusion polypeptide comprising an amino acid sequence of any of a) to c).

In another embodiment, the selective $p75^{NTR}$ antagonists include the peptide CFFRGGFFNHNPRYC (SEQ ID NO: 9) or b) a functional fragment of a); c) a functional homolog of a) or b) or functional fragment thereof; and d) a fusion polypeptide comprising an amino acid sequence of any of a) to c).

In accordance with a further embodiment, the invention provides a selective $p75^{NTR}$ antagonist wherein the antagonist is a polypeptide comprising the amino acid sequence CATDIKGAEC (SEQ ID NO: 1), or ATLDALLAALRRIQ (SEQ ID NO: 8), or CFFRGGFFNHNPRYC (SEQ ID NO: 9), or a combination of two or more of said peptides.

The term, "amino acid" includes the residues of the natural α-amino acids (e.g., Ala, Arg, Asn, Asp, Cys, Glu, Gln, Gly, His, Lys, Ile, Leu, Met, Phe, Pro, Ser, Thr, Trp, Tyr, and Val) in D or L form, as well as β-amino acids, synthetic and non-natural amino acids. Many types of amino acid residues are useful in the polypeptides and the invention is not limited to natural, genetically-encoded amino acids. Examples of amino acids that can be utilized in the peptides described herein can be found, for example, in Fasman, 1989, CRC Practical Handbook of Biochemistry and Molecular Biology, CRC Press, Inc., and the reference cited therein. Another source of a wide array of amino acid residues is provided by the website of RSP Amino Acids LLC.

Reference herein to "derivatives" includes parts, fragments and portions of the inventive selective $p75^{NTR}$ antagonist peptides. A derivative also includes a single or multiple amino acid substitution, deletion and/or addition. Homologues include functionally, structurally or stereochemically similar peptides which bind helix 5 of the six α-helices of the intracellular domain of $p75^{NTR}$ from the same species of mammal or from within the same genus or family of mammals. All such homologues are contemplated by the present invention.

Analogs and mimetics include molecules which include molecules which contain non-naturally occurring amino acids or which do not contain amino acids but nevertheless behave functionally the same as the peptide.

Examples of incorporating non-natural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A partial list of known non-natural amino acid contemplated herein is shown in Table 1.

TABLE 1

| Non-natural Amino Acids | | | |
|---|---|---|---|
| Non-conventional amino acid | Code | Non-conventional amino acid | Code |
| α-aminobutyric acid | Abu | L-N-methylalanine | Nmala |
| α-amino-a-methylbutyrate | Mgabu | L-N-methylarginine | Nmarg |
| aminocyclopropane-carboxylate | Cpro | L-N-methylasparagine | Nmasn |
| | | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
| | | L-N-methylglutamic acid | Nmglu |
| cyclohexylalanine | | Chexa L-N-methylhistidine | Nmhis |
| cyclopentylalanine | Cpen | L-N-methylisolleucine | Nmile |
| D-alanine | Dal | L-N-methylleucine | Nmleu |

TABLE 1-continued

Non-natural Amino Acids

| Non-conventional amino acid | Code | Non-conventional amino acid | Code |
|---|---|---|---|
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methyloniithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) | Nnbhm | N-(N-(3,3-diphenylpropyl) | Nnbhe |

TABLE 1-continued

Non-natural Amino Acids

| Non-conventional amino acid | Code | Non-conventional amino acid | Code |
|---|---|---|---|
| carbamylmethyl)glycine | | carbamylmethyl)glycine | |
| 1-carboxy-1-(2,2-diphenyl-ethylamino)cyclopropane | Nmbc | | |

Analogs of the subject peptides contemplated herein include modifications to side chains, incorporation of non-natural amino acids and/or their derivatives during peptide synthesis and the use of crosslinkers and other methods which impose conformational constraints on the peptide molecule or their analogs.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention further contemplates small chemical analogs of the subject peptides capable of acting as antagonists which bind helix 5 of the six α-helices of the intracellular domain of $p75^{NTR}$. Chemical analogs may not necessarily be derived from the peptides themselves but may share certain conformational similarities. Alternatively, chemical analogs may be specifically designed to mimic certain physiochemical properties of the peptides. Chemical analogs may be chemically synthesized or may be detected following, for example, natural product screening.

The term, "peptide," as used herein, includes a sequence of from four to 100 amino acid residues in length, preferably about 10 to 80 residues in length, more preferably, 15 to 65 residues in length, and in which the α-carboxyl group of one amino acid is joined by an amide bond to the main chain (α- or (β-) amino group of the adjacent amino acid. The peptides provided herein for use in the described and claimed methods and compositions can also be cyclic.

The precise effective amount for a human subject will depend upon the severity of the subject's disease state, general health, age, weight, gender, diet, time and frequency of administration, drug combination(s), reaction sensitivities, and tolerance or response to therapy. A routine experimentation can determine this amount and is within the judgment of the medical professional. Compositions may be administered individually to a patient, or they may be administered in combination with other drugs, hormones, agents, and the like.

As used herein, the term "$p75^{NTR}$ antagonists" has its usual meaning and in general, means a biologically active agent, such as any ligand, protein, peptide, small molecule, antibody, or peptidomimetic which selectively binds $p75^{NTR}$ but does not elicit the functional response of the receptor, e.g., reduce contractility or relaxation or increase adverse cardiac remodeling.

The term "ligand" refers to molecules that bind to the $p75^{NTR}$ via the segments involved in peptide ligand binding. Also, a ligand is a molecule which serves either as a natural ligand to which the receptor, or an analog thereof, binds, or a molecule which is a functional analog of a natural ligand. The functional analog may be a ligand with structural modifications, or may be a wholly unrelated molecule which has a molecular shape which interacts with the appropriate ligand binding determinants. The ligands may serve as agonists or antagonists, see, e.g., Goodman, et al. (eds.) (1990) Goodman & Gilman's: The Pharmacological Bases of Therapeutics (8th ed.), Pergamon Press.

Thus, in accordance with an embodiment, the present invention provides a method for increasing contractility in a cardiac cell or population of cells comprising contacting the cell or population of cells with a composition comprising an effective amount of at least one $p75^{NTR}$ antagonist.

In accordance with another embodiment, the present invention provides a method for increasing contractility in a cardiac cell or population of cells comprising contacting the cell or population of cells with a composition comprising an effective amount of at least one p75$^{NTR}$ antagonist and at least one additional biologically active agent.

In accordance with an embodiment, the present invention provides for the use of the pharmaceutical composition comprising an effective amount of at least one p75$^{NTR}$ antagonist, for improving contractility in cardiac tissue of a subject comprising administering to the subject an effective amount of the pharmaceutical composition comprising an effective amount of at least one p75$^{NTR}$ antagonist.

In some embodiments of the above use, the composition comprises at least one additional cardiotropic agent.

In accordance with another embodiment, the present invention provides for the use of the pharmaceutical composition comprising an effective amount of at least one p75$^{NTR}$ antagonist, for treating congestive heart failure in a subject comprising administering to the subject an effective amount of the pharmaceutical composition comprising an effective amount of at least one p75$^{NTR}$ antagonist.

In some embodiments of the above use, the composition comprises at least one additional cardiotropic agent.

An active agent, therapeutic agent, and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

The biologically active agent may vary widely with the intended purpose for the composition. The term active is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released the subject composition, for example, into adjacent tissues or fluids upon administration to a subject.

Further examples of biologically active agents include, without limitation, enzymes, receptor antagonists or agonists, hormones, growth factors, autogenous bone marrow, antibiotics, antimicrobial agents, and antibodies.

A particular example of biologically active agents includes "cardiotropic" agents. As defined herein, "cardiotropic" agents comprise cardiac glycosides, β-blockers, calcium channel blockers, nitrates, class I antiarrhythmics, class antiarrhythmics II, angiotensin-converting enzyme inhibitor (ACE inhibitor) antihypertensives, central-acting adrenergic antihypertensives, diuretic antihypertensive agents, and peripheral vasodilator antihypertensives.

Further examples of cardiotropic agents includes cholinergic agonist parasympathomimetics, cholinesterase inhibitor parasympathomimetics, sympatholytics, α-blocker sympatholytics, sympatholytics, sympathomimetics, and adrenergic agonist sympathomimetics; cardiovascular agents, such as antianginals, antianginals, calcium-channel blocker antianginals, nitrate antianginals, antiarrhythmics, cardiac glycoside antiarrhythmics, class III antiarrhythmics, class IV antiarrhythmics, α-blocker antihypertensives, β-blocker antihypertensives, angiotensin-converting enzyme inhibitor (ACE inhibitor) antihypertensives, 13-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, reductase inhibitor antilipemics, inotropes, cardiac glycoside inotropes, and thrombolytic agents.

Specific examples of cardiotropic agents include cardiovascular agents, such as aspirin (ASA) (enteric coated ASA); β-blocker antianginals, such as atenolol and propranolol; calcium-channel blocker antianginals, such as nifedipine and verapamil; nitrate antianginals, such as isosorbide dinitrate (ISDN); cardiac glycoside antiarrhythmics, such as class I antiarrhythmics, such as lidocaine, mexiletine, phenytoin, procainamide, and quinidine; class antiarrhythmics II, such as atenolol, metoprolol, propranolol, and timolol; class III antiarrhythmics, such as amiodarone; class IV antiarrhythmics, such as diltiazem and verapamil; antihypertensives, such as prazosin; angiotensin-converting enzyme inhibitor (ACE inhibitor) antihypertensives, such as captopril and enalapril; antihypertensives, such as atenolol, metoprolol, nadolol, and propanolol; calcium-channel blocker antihypertensive agents, such as diltiazem and nifedipine; central-acting adrenergic antihypertensives, such as clonidine and methyldopa; diuretic antihypertensive agents, such as amiloride, furosemide, hydrochlorothiazide (HCTZ), and spironolactone; peripheral vasodilator antihypertensives, such as minoxidil; antilipemics, such as gemfibrozil and probucol; bile acid sequestrant antilipemics, such as cholestyramine; reductase inhibitor antilipemics, such as lovastatin and pravastatin; inotropes, such as amrinone, dobutamine, and dopamine; cardiac glycoside inotropes, such as thrombolytic agents, such as alteplase, anistreplase, streptokinase, and urokinase.

Routes of administration of the inventive peptides include, but are not limited to intravenously, intraperitioneal, subcutaneously, intracranial, intradermal, intramuscular, intraocular, intrathecal, intracerebrally, intranasally, infusion, orally, rectally, via iv drip, patch and implant.

In one or more embodiments, the present invention provides pharmaceutical compositions comprising one or more of the inventive peptides and a pharmaceutically acceptable carrier. In other aspects, the pharmaceutical compositions also include one or more additional biologically active agents.

With respect to peptide compositions described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, or suspensions. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

In addition, in an embodiment, the compositions comprising the inventive peptides or derivatives thereof, may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular peptide containing compositions, as well as by the particular method used to administer the composition. Accordingly, there are a variety of suitable formulations of the pharmaceutical compositions of the invention. More than one route can be used to administer the compositions of the present invention, and in certain instances, a particular route can provide a more immediate and more effective response than another route.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect.

More specifically, the pharmaceutical compositions of the present invention may be administered in a single daily dose, or the total daily dosage may be administered in divided doses of two, three, or four times daily. In the case of oral administration, the daily dosage of the compositions may be varied over a wide range from about 0.1 ng to about 1,000 mg per patient, per day. The range may more particularly be from about 0.001 ng/kg to 10 mg/kg of body weight per day, about 0.1-100 μg, about 1.0-50 μg or about 1.0-20 mg per day for adults (at about 60 kg).

The daily dosage of the pharmaceutical compositions may be varied over a wide range from about 0.1 ng to about 1000 mg per adult human per day. For oral administration, the compositions may be provided in the form of tablets containing from about 0.1 ng to about 1000 mg of the composition or 0.001, 0.002, 0.003, 0.004, 0.005, 0.01, 0.05, 0.1, 0.2, 0.5, 1.0, 2.0, 5.0, 10.0, 15.0, 100, 150, 200, 250, 300, 350, 400, 450, 500, 550, 600, 650, 700, 800, 900, or 1000 milligrams of the composition for the symptomatic adjustment of the dosage to the patient to be treated. An effective amount of the pharmaceutical composition is ordinarily supplied at a dosage level of from about 0.1 ng/kg to about 20 mg/kg of body weight per day. In one embodiment, the range is from about 0.2 ng/kg to about 10 mg/kg of body weight per day. In another embodiment, the range is from about 0.5 ng/kg to about 10 mg/kg of body weight per day. The pharmaceutical compositions may be administered on a regimen of about 1 to about 10 times per day.

In the case of injections, it is usually convenient to give by an intravenous route in an amount of about 0.0001 μg-30 mg, about 0.01 μg-20 mg or about 0.01-10 mg per day to adults (at about 60 kg). In the case of other animals, the dose calculated for 60 kg may be administered as well. More specifically, in the case of injections, it is usually convenient to give pharmaceutical compositions by a subcutaneous route in an amount of about 0.01 mg/kg to about 0.5 mg/kg of pharmaceutical compositions, more specifically, about 0.01 mg/kg to 0.5 mg/kg, about 0.02 mg/kg to about 0.5 mg/kg, about 0.03 mg/kg to about 0.5 mg/kg, about 0.04 mg/kg to about 0.45 mg/kg, about 0.06 mg/kg to about 0.45 mg/kg, about 0.07 mg/kg to about 0.4 mg/kg, about 0.08 mg/kg to about 0.35 mg/kg, about 0.09 mg/kg to about 0.3 mg/kg, about 0.1 mg/kg to about 0.25 mg/kg, and so on.

Doses of a pharmaceutical composition of the present invention can optionally include 0.0001 μg to 1,000 mg/kg/administration, or 0.001 μg to 100.0 mg/kg/administration, from 0.01 μg to 10 mg/kg/administration, from 0.1 μg to 10 mg/kg/administration, including, but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 μg/ml serum concentration per single or multiple administration or any range, value or fraction thereof.

As a non-limiting example, treatment of subjects can be provided as a one-time or periodic dosage of a composition of the present invention 0.1 ng to 100 mg/kg such as 0.0001, 0.001, 0.01, 0.1 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Specifically, the pharmaceutical compositions of the present invention may be administered at least once a week over the course of several weeks. In one embodiment, the pharmaceutical compositions are administered at least once a week over several weeks to several months. In another embodiment, the pharmaceutical compositions are administered once a week over four to eight weeks. In yet another embodiment, the pharmaceutical compositions are administered once a week over four weeks.

More specifically, the pharmaceutical compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

Alternatively, the pharmaceutical compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days.

The pharmaceutical compositions of the present invention may alternatively be administered about once every week, about once every 2 weeks, about once every 3 weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks.

Alternatively, the pharmaceutical compositions of the present invention may be administered about once every month, about once every 2 months, about once every 3 months, about once every 4 months, about once every 5 months, about once every 6 months, about once every 7 months, about once every 8 months, about once every 9 months, about once every 10 months, about once every 11 months, or about once every 12 months.

Alternatively, the pharmaceutical compositions may be administered at least once a week for about 2 weeks, at least once a week for about 3 weeks, at least once a week for about 4 weeks, at least once a week for about 5 weeks, at least once a week for about 6 weeks, at least once a week for about 7 weeks, at least once a week for about 8 weeks, at least once a week for about 9 weeks, at least once a week for about 10 weeks, at least once a week for about 11 weeks, at least once a week for about 12 weeks, at least once a week for about 13 weeks, at least once a week for about 14 weeks, at least once a week for about 15 weeks, at least once a week for about 16 weeks, at least once a week for about 17 weeks, at least once a week for about 18 weeks, at least once a week for about 19 weeks, or at least once a week for about 20 weeks.

Alternatively the pharmaceutical compositions may be administered at least once a week for about 1 month, at least once a week for about 2 months, at least once a week for about 3 months, at least once a week for about 4 months, at least once a week for about 5 months, at least once a week for about 6 months, at least once a week for about 7 months, at least once a week for about 8 months, at least once a week for about 9 months, at least once a week for about 10 months, at least once a week for about 11 months, or at least once a week for about 12 months.

As used herein, the term "treat," as well as words stemming therefrom, includes diagnostic and preventative as well as disorder remitative treatment.

By "disease" is meant any condition or disorder which damages or interferes with the normal function of a cell, tissue, or organ. Examples of such diseases include: heart failure secondary, but not limited to, coronary artery disease, hypertension, valvular defects, arrhythmias, conduction disturbances and idiopathic cardiomyopathies, as well as atherosclerosis, inflammatory diseases such as rheumatoid arthritis, infectious diseases, amyloidosis or Marfan's syndrome, collagen vascular disease, cancer therapies or other conditions which predispose the heart to failure.

The failing, overloaded heart is characterized by a progressive dilatation (adverse remodeling), myocardial apoptosis and necrosis and reduced contractility. The latter can be defined as the relative ability of the heart to eject a stroke volume (SV) at a given prevailing afterload (arterial pressure) and preload (end-diastolic volume; EDV).

By "an effective amount" is meant the amount required to identify, diagnose, image, or ameliorate the symptoms of a disease relative in an untreated or treated patient. The effective amount of active compound(s) used to practice the present invention for therapeutic treatment of a cardiac disease varies depending upon the manner of administration, the age, body weight, and general health of the subject. Ultimately, the attending physician or veterinarian will decide the appropriate amount and dosage regimen. Such amount is referred to as an "effective" amount. In a preferred embodiment, the disease is heart failure.

"Antioxidant" as used herein is understood as a molecule capable of slowing or preventing the oxidation of other molecules. Oxidation is a chemical reaction that transfers electrons from a substance to an oxidizing agent. Such reactions can be promoted by or produce superoxide anions or peroxides. Oxidation reactions can produce free radicals, which start chain reactions that damage cells. Antioxidants terminate these chain reactions by removing free radical intermediates, and inhibit other oxidation reactions by being oxidized themselves. As a result, antioxidants are often reducing agents such as thiols, ascorbic acid or polyphenols. Antioxidants include, but are not limited to, α-tocopherol, ascorbic acid, Mn(III)tetrakis (4-benzoic acid) porphyrin, α-lipoic acid, and n-acetylcysteine.

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In accordance with an embodiment, the present invention provides a method for identifying a target molecule as having $p75^{NTR}$ antagonist activity in vitro comprising: a) contacting one or more isolated cardiac myocytes with a solution comprising a target molecule or a control solution; b) contacting the isolated cardiac myocytes of a) contacted with the solution comprising the target molecule, or contacted with the control solution with a solution comprising an effective amount of proBDNF; c) generating images of the isolated cardiac myocytes using fluorescence microscopy; d) measuring contractility from the images of c); and e) identifying the target molecule as having $p75^{NTR}$ antagonist when the amount of contractility and/or relaxation is increased in the isolated cardiac myocytes contacted with the solution comprising the target molecule relative to the isolated cardiac myocytes contacted with the control solution.

In accordance with another embodiment, the present invention provides a method for identifying a target molecule as having $p75^{NTR}$ antagonist activity in vitro comprising: a) loading one or more isolated cardiac myocytes with a solution comprising a calcium sensitive dye fluorescent dye; b) contacting the one or more isolated cardiac myocytes of a) with a solution comprising a target molecule or a control solution; c) contacting the isolated cardiac myocytes of b) contacted with the solution comprising the target molecule, or contacted with the control solution with a solution comprising an effective amount of proBDNF; d) generating images of the isolated cardiac myocytes using confocal laser scanning microscopy; e) measuring $Ca^{2+}$ transient flux from the images of d); and f) identifying the target molecule as having $p75^{NTR}$ antagonist activity when the amount of $Ca^{2+}$ transient flux is increased in the isolated cardiac myocytes contacted with the solution comprising the target molecule relative to the isolated cardiac myocytes contacted with the control solution.

In some embodiments, the present invention provides a screening assay comprising a plurality of mice which have heart failure that was induced by transverse aortic constriction (TAC), simulating aortic stenosis that are treated with a compound of interest are compared to a plurality of mice which have heart failure that was induced by TAC that are treated with a control composition, wherein the TAC mice are used to measure in vivo pressure-volume relationships to determine load-independent indexes of myocardial contractility and in vivo remodeling, testing the impact of the above mentioned interventions on in vivo heart function and response to chronic stressing conditions.

In accordance with some embodiments, the whole heart preparations or in vivo preparations used in the assays to test the impact of the above mentioned potential $p75^{NTR}$ antagonists on hearts isolated from TAC or infarcted mice, and evaluating whether the target molecules are $p75^{NTR}$ antagonists.

In some embodiments, these mice can be treated in vivo with target molecules or controls for a period of time and then in vivo heart function is studied monitoring load-independent indexes of myocardial contractility via pressure-volume relationships. In addition, hearts are isolated from previously in vivo treated mice and studied for changes in coronary vascular function, left-ventricle function and/or relaxation according to the Langendorff procedure. The use of isolated, Langendorff-perfused hearts will also enable studying molecular and biochemical mechanisms of HF-induced adverse remodeling, cardiac pump dysfunction, increase in oxidative stress and myocardial cell death/apoptosis. In alternative embodiments, these mice will not be treated in vivo, but the heart preparations from the TAC and infarct mice are then tested with the target molecules and compared to control mice hearts.

As such, in accordance with a further embodiment, the present invention provides a method for identifying a target molecule as having $p75^{NTR}$ antagonist activity in a whole heart preparation in vitro comprising: a) contacting one or more whole heart preparations with a solution comprising a target molecule or a control solution; b) contacting the whole heart preparations of a) contacted with the solution comprising the target molecule, or contacted with the control solution with a solution comprising an effective amount of proBDNF; c) measuring coronary perfusion pressure and/or left-ventricle function and/or relaxation in the whole heart preparations of b); and d) identifying the target molecule as having p75$^{NTR}$ antagonist when the amount of contractility and/or relaxation is increased, or the amount of adverse cardiac remodeling is decreased, in the whole heart preparations of b) contacted with the solution comprising the target molecule relative to the isolated cardiac myocytes contacted with the control solution.

In accordance with another embodiment, the present invention provides a method for identifying a target molecule as having p75$^{NTR}$ antagonist activity in vivo comprising: a) administering to one or more mammals a composition comprising one or more target molecules or controls for a period of time; b) measuring in vivo heart function of the mammals in a) including load-independent indexes of myocardial contractility via pressure-volume relationships; and c) identifying the one or more target molecules as having p75$^{NTR}$ antagonist when the amount of contractility and/or relaxation is increased in the mammals administered the one or more target molecules, when compared to the amount of contractility and/or relaxation in the mammals administered the controls.

The compounds tested novel compounds of interest for their effect on the increase or decrease in contractility and/or relaxation, or Ca$^{2+}$ transient flux, can be any small chemical compound, or a biological entity, such as, without limitation, include small organic molecules, peptides, proteins, oligonucleotides, aptamers, antibodies, and siRNAs, saccharides, nucleic acids, lipids, enzymes, receptor antagonists or agonists, hormones, growth factors, antibiotics, antimicrobial agents, and antibodies. Typically, test compounds will be small synthetic and natural molecules and peptides or antibodies.

EXAMPLES

Confocal Immunohistochemistry.

Mouse adult ventricular myocytes were isolated, fixed, and stained for confocal immunohistochemistry as previously (Circ. Res., 2007; 100(1):96-104; Proc. Natl. Acad. Sci. USA 2015). Cells were fixed with 50% methanol and 50% acetone, permeabilized with 0.1% saponin in PBS, blocked in 10% BSA in PBS, incubated overnight with primary antibodies at 4° C. (Advanced Targeting Systems, Cat # AB-N01) and subsequently incubated with secondary antibodies for 1 h at room temperature (Alexa Fluor 488-conjugated donkey anti-rabbit; Invitrogen). Imaging was performed using an argon-krypton laser confocal scanning microscope (UltraView; Perkin Elmer Life Science Inc.).

Cardiac Myocyte Isolation.

Isolation of rat and mouse ventricular myocytes was carried out as previously described and approved by the Animal Care and Use Committee of Johns Hopkins University. Mice were anesthetized with intraperitoneal pentobarbital sodium (100 mg/kg). To assess for sarcomere shortening, cells were imaged using field stimulation (0.5 Hz) in an inverted fluorescence microscope (Diaphot 200; Nikon, Inc). Sarcomere length was measured by real-time Fourier transform (IonOptix MyoCam, CCCD100M). Twitch amplitude is expressed as a percentage of resting cell length. Twitch kinetics was quantified by measuring the time to peak shortening and the time from peak shortening to 50% relaxation. For whole Ca$^{2+}$ transient measurements, myocytes were loaded with the Ca$^{2+}$ indicator fluo-4/A M (Molecular Probes, 20 μM for 30 min) and Ca$^{2+}$ transients were measured under field-stimulation (0.5 Hz) in perfusion solution by confocal laser scanning microscope (LSM510, Carl Zeiss). Digital image analysis used customer-designed programs coded in Interactive Data Language (IDL).

Transverse Aortic Constriction to induce Pressure Overload/Heart Failure and P75NTR Antagonist Infusion.

Transverse aortic constriction (TAC) was performed following a previously reported protocol (J. Clin. Invest., 2005; 115(5):1221-31; Circ. Res., 2010; 106(1):193-202; Antioxid Redox Signal 2014; 20(2):267-80). After induction of anesthesia and intubation, mice were placed on a volume ventilator (120 breaths/min, 1.2 ml/g/min) and anesthesia was maintained with 5% isofluorane. The aortic arch was isolated and tied against a 27-gauge needle, resulting in a 65-70% constriction after the removal of the needle. The chest and skin were closed and animals extubated and allowed to fully recover. Sham-operated mice underwent the same operation except that after the aortic arch was isolated, no ligature was placed. The ALZET osmotic pump (Model 2004) with P75$^{NTR}$ peptidic antagonist (200 μg/kg/day) or saline vehicle was placed subcutaneously one week after TAC. P75$^{NTR}$ antagonistic cyclic peptide (CATDIKGAEC) (SEQ ID NO: 1) was synthesized at the Johns Hopkins Synthesis and Sequencing Facility. The Johns Hopkins University Institutional Animal Care and Use Committee approved all animal experiments, which conformed to the guidelines from the National Institutes of Health.

Echocardiography.

In vivo cardiac morphology and function were assessed by serial M-mode echocardiography (Acuson Sequioa C256, 13 MHz transducer, Siemens, Pa.) performed in conscious mice. LV end-systolic and end-diastolic dimensions were averaged from 3-5 beats. LV percent FS, EF and LV mass were calculated as described previously. Thickness of posterior free wall and interventricular septum were averaged.

Assessment of left ventricular [LV] function and coronary tone in Langendorff-perfused hearts.

After anesthesia, hearts were harvested and the aorta cannulated and retrogradely perfused with Krebs-Henseleit (KH) buffer warmed and gassed with 95% $O_2$ and 5% $CO_2$, as reported previously (Antioxid. Redox Signal, 2013; 19(11):1185-97). Briefly, hearts were paced at 600 bpm (10 Hz, 4 ms duration, 4 V) and LV function monitored with a water-filled balloon, connected to a pressure transducer coupled to a continuous data recording system. After stabilization, in addition to LV function parameters, baseline values of coronary perfusion pressure (CPP) were obtained through a side-arm of the aortic cannula connected to a separate pressure transducer.

Statistical analysis.

Results are expressed as means±SEM. Significance was estimated by one-way repeated measures ANOVA and/or Student's t-test for paired observations as appropriate. P≤0.05 was considered significant.

Example 1

Figure 2A:
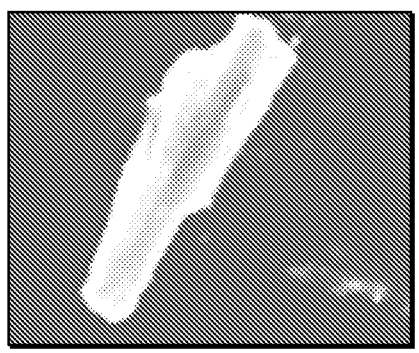
FIGS. 2A-2E show $p75^{NTR}$, NRIF and sortilin expression in adult (or neonatal) mouse ventricular myocytes from WT mice (A) and total $p75^{NTR-/-}$ mice, at baseline and after TAC
Figure 2B:
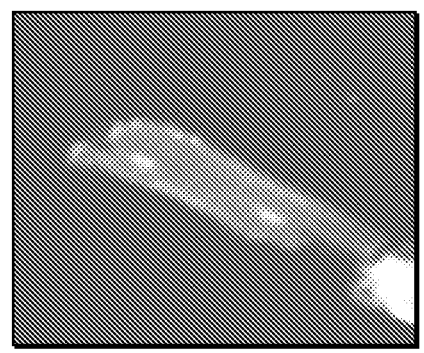
Figure 2C:
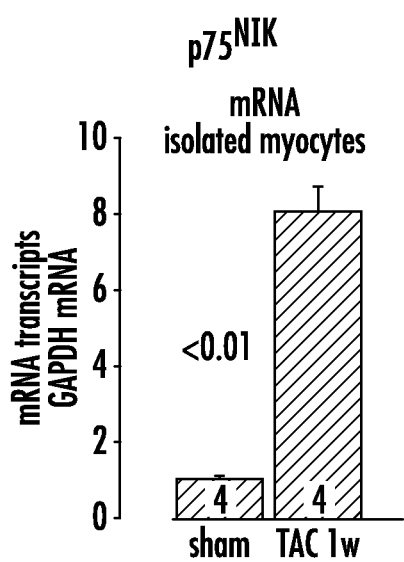
Figure 2D:
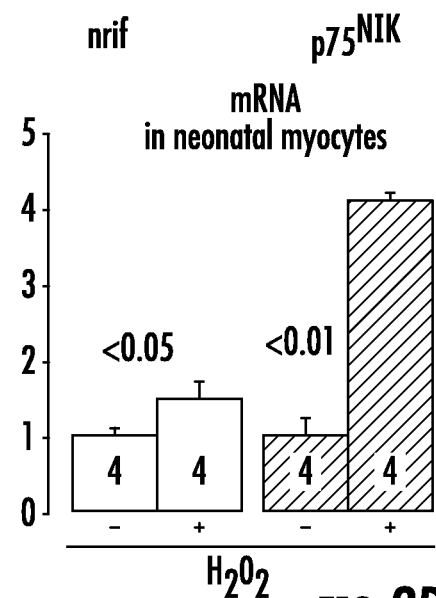
Figure 2E:
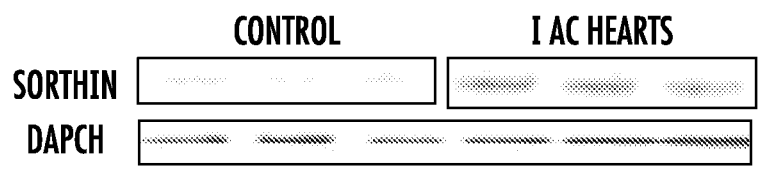

In FIG. 2A, we report that p75$^{NTR}$ is lined-up on the sarcolemma of an isolated normal mouse ventriculocyte; conversely, this staining is totally absent in a p75$^{NTR-/-}$ cardiac cells (FIG. 2B, mice generated in our lab). Elements of the p75$^{NTR}$ signaling cascade depicted in FIG. 1 are detectable, at gene expression level, in isolated ventricular myocytes, thus away from any possible contamination from neighboring vessels and nerves in which p75$^{NTR}$ could be also present (FIGS. C-E). Moreover, insults such as pressure overload (TAC) or oxidative stress (via $H_2O_2$) led to their up-regulation.

Example 2

Figure 3:
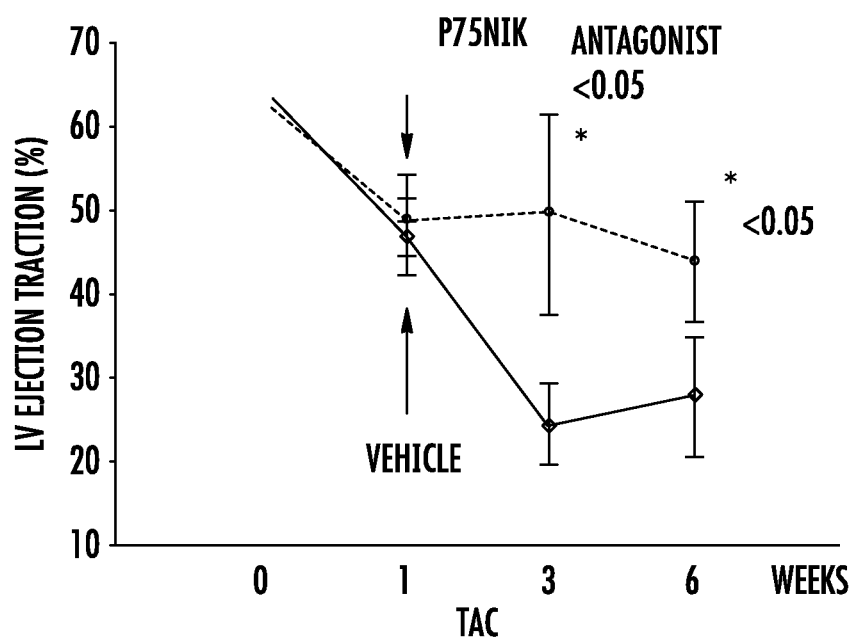
FIG. 3 depicts the impact of $p75^{NTR}$ antagonist (or vehicle=saline) on left ventricular function after transverse aortic constriction.

The chronic infusion of the cyclic peptide CATDIKGAEC (SEQ ID NO: 1) (for 5 weeks, instituted 1 week after TAC) preserved LV ejection fraction (FIG. 3), suggesting the ability of $p75^{NTR}$ antagonists to counter LV dysfunction in mice with hemodynamic stress. A cause-effect relationship between the presence of proBDNF, $p75^{NTR}$ activation and myocardial dysfunction is suggested by our data obtained in Langendorff perfused hearts. When infused in control mouse hearts, proBDNF induced vasoconstriction as reflected in the markedly higher coronary perfusion pressure (CPP, FIG. 4A), while reducing overall left-ventricle (LV) function, both in terms of contractility (FIGS. 4B,D and E) and relaxation (FIG. 4F). Although the mechanisms of proBDNF induced deterioration remain to be elucidated, our data show that it can affect both vascular (FIG. 4A) and myocyte function.

Example 3

Figure 5:
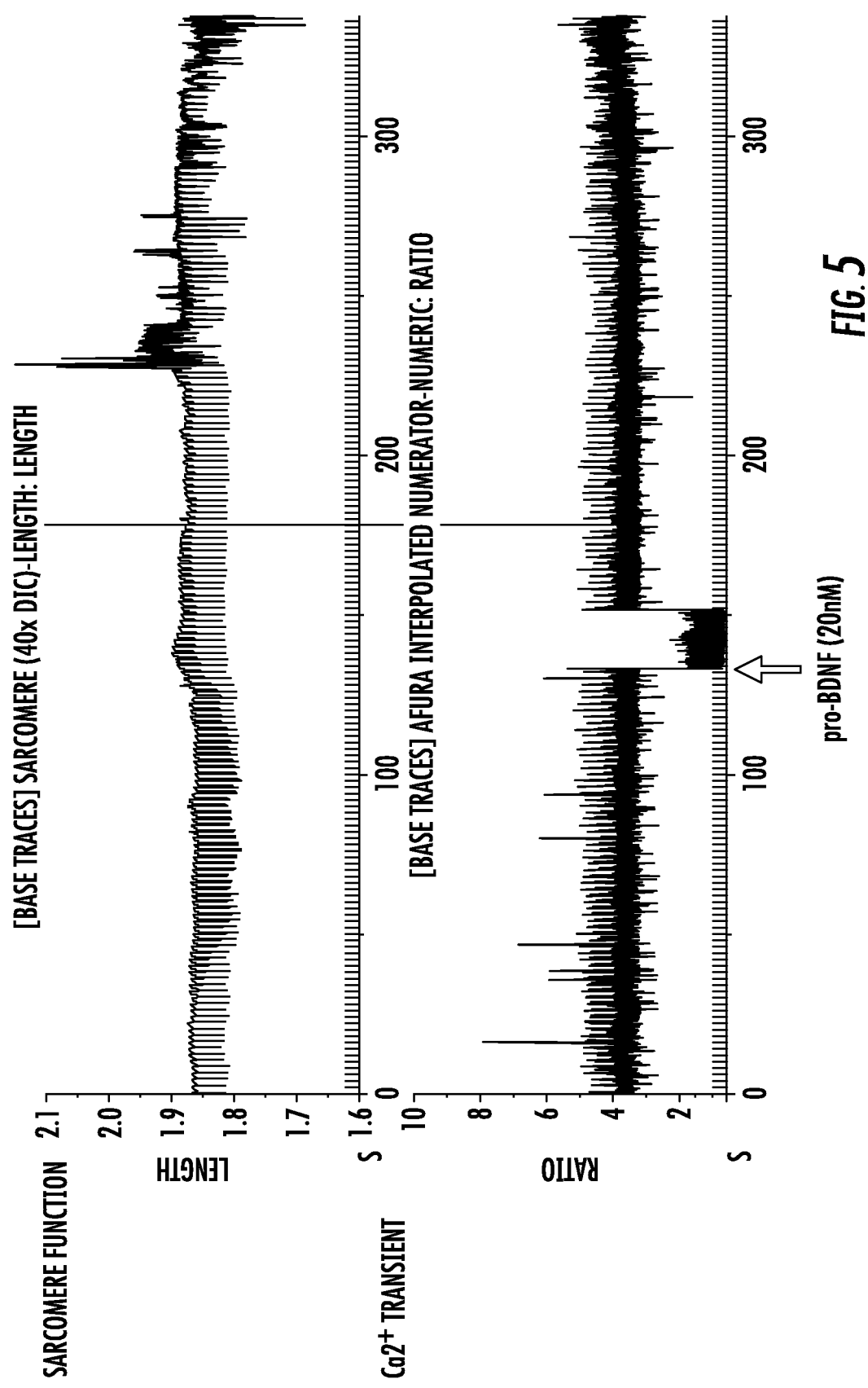
FIG. 5 shows the impact of proBDNF infusion on the function of isolated normal murine myocytes (cell #1).
Figure 6:
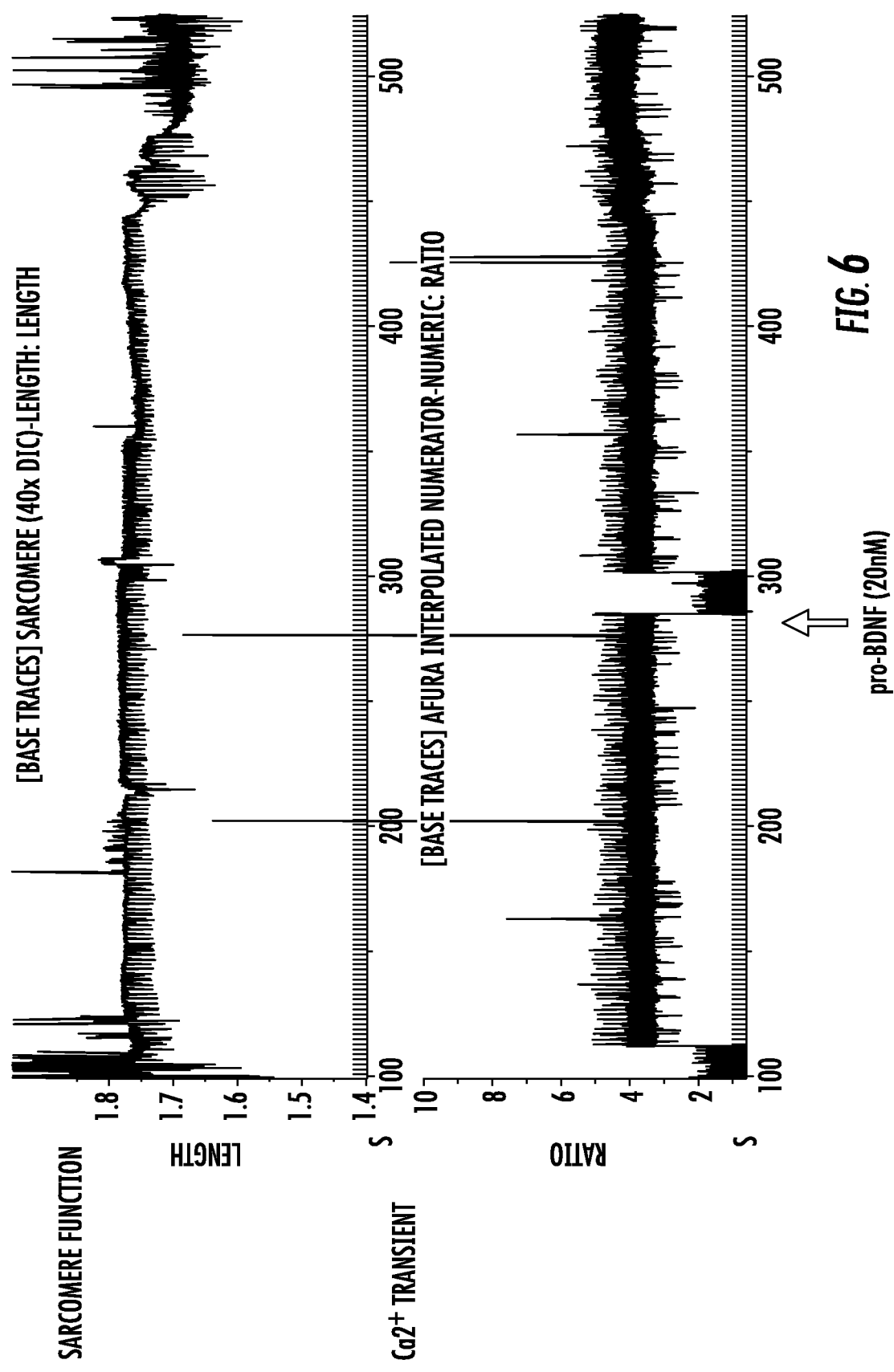
FIG. 6 shows the impact of proBDNF infusion on the function of isolated normal murine myocytes (cell #2).
Figure 7:
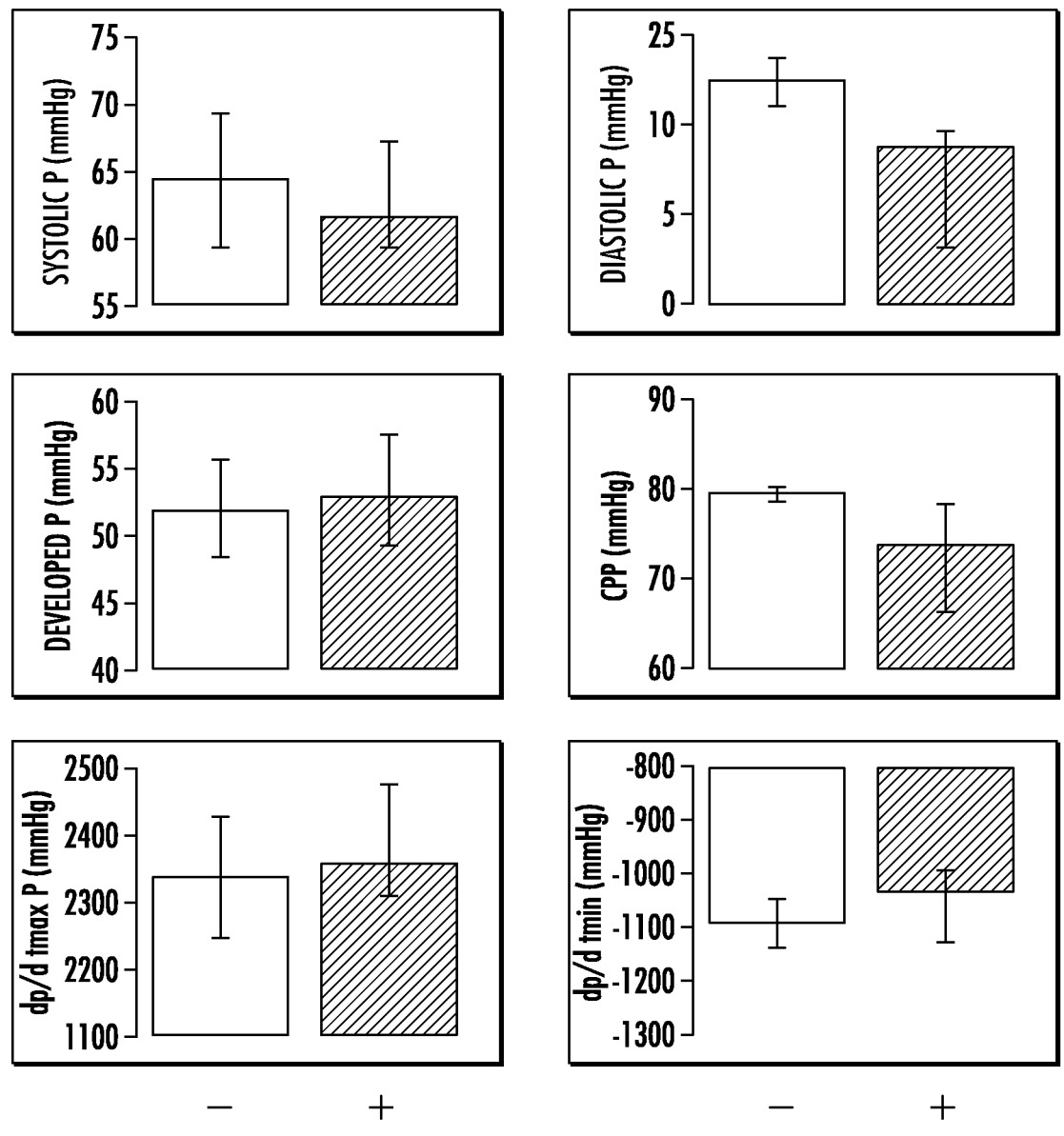
FIG. 7 shows the impact of proBDNF infusion on isolated $p75^{NTR-/-}$ mouse heart function.

The latter eventuality is supported by additional data in isolated myocytes (FIGS. 5 and 6) showing that, when directly applied to isolated healthy mouse myocytes, proBDNF reduces contractility (extent of sarcomere shortening, upper panels) and amplitude of the whole $Ca^{2+}$ transient, with a rise in diastolic $Ca^{2+}$ levels (lower panels). The specificity of proBDNF and $p75^{NTR}$ interaction is suggested by studies done in isolated $p75^{NTR-/-}$ whole hearts. As shown in FIG. 7, proBDNF does not alter LV function or coronary vascular tone in mice lacking $p75^{NTR}$. The data demonstrate that antagonizing $p75^{NTR}$, whose expression/activity can be up-regulated in hemodynamically stressed (and prone to failure) hearts, improves function, likely preventing or retarding HF progression. Moreover, here we provide evidence that proBDNF activates cardiac $p75^{NTR}$-dependent pathways, leading to acute alterations in coronary vascular tone and myocardial contractility. Hence, interventions aiming at countering both $p75^{NTR}$ activation or correcting deficient enzymatic conversion of proBDNF to mature BDNF constitute, alone or in combination, a new therapeutic strategy to counter loss of function, and likely adverse remodeling, in hearts subject to acute or chronic hemodynamic stress of different etiology.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A pharmaceutical composition comprising a 75 kD transmembrane neurotrophin receptor (p75$^{NTR}$) antagonist peptide consisting of the sequence ATLDALLAALRRIQ (SEQ ID NO: 8) and one or more additional (p75$^{NTR}$) antagonist peptides having the sequence selected from the group consisting of: CATDIKGAEC (SEQ ID NO: 1), and CFFRGGFFNHNPRYC (SEQ ID NO: 9) and a pharmaceutically acceptable carrier.

2. The pharmaceutical composition of claim 1, wherein the composition comprises at least one additional cardiotropic agent.

3. The pharmaceutical composition of claim 2, wherein the cardiotropic agent is selected from the group consisting of cardiac glycosides, β-blockers, calcium channel blockers, nitrates, class I antiarrhythmics, class II antiarrhythmics, angiotensin-converting enzyme inhibitor (ACE inhibitor) antihypertensives, central-acting adrenergic antihypertensives, diuretic antihypertensive agents, and peripheral vasodilator antihypertensives.

4. A method for improving contractility in cardiac tissue of a subject comprising administering to the subject an effective amount of the pharmaceutical composition of claim 1.

5. The method of claim 4, wherein the composition comprises at least one additional cardiotropic agent.

6. A method for treating congestive heart failure in a subject who has congestive heart failure comprising administering to the subject an effective amount of the pharmaceutical composition of claim 1.

7. The method of claim 6, wherein the composition comprises at least one additional cardiotropic agent.

8. A method for improving contractility in cardiac tissue of a subject in need thereof comprising administering to the subject an effective amount of the pharmaceutical composition of claim 1.

9. The method of claim 8, wherein the composition comprises at least one additional cardiotropic agent.

10. The method of claim 5, wherein the cardiotropic agent is selected from the group consisting of cardiac glycosides, β-blockers, calcium channel blockers, nitrates, class I antiarrhythmics, class II antiarrhythmics, angiotensin-converting enzyme inhibitor (ACE inhibitor) antihypertensives, central-acting adrenergic antihypertensives, diuretic antihypertensive agents, and peripheral vasodilator antihypertensives.

11. The method of claim 9, wherein the cardiotropic agent is selected from the group consisting of cardiac glycosides, β-blockers, calcium channel blockers, nitrates, class I antiarrhythmics, class II antiarrhythmics, angiotensin-converting enzyme inhibitor (ACE inhibitor) antihypertensives, central-acting adrenergic antihypertensives, diuretic antihypertensive agents, and peripheral vasodilator antihypertensives.

12. A method for improving contractility in cardiac tissue of a subject in need thereof comprising administering to the subject an effective amount of a pharmaceutical composition comprising one or more 75 kD transmembrane neurotrophin receptor (p75$^{NTR}$) antagonist peptides having the sequence selected from the group consisting of: CATDIKGAEC (SEQ ID NO: 1), ATLDALLAALRRIQ (SEQ ID NO: 8) and CFFRGGFFNHNPRYC (SEQ ID NO: 9).

13. The method of claim 12, wherein the composition comprises at least one additional cardiotropic agent.

14. The method of claim 13, wherein the cardiotropic agent is selected from the group consisting of cardiac glycosides, β-blockers, calcium channel blockers, nitrates, class I antiarrhythmics, class II antiarrhythmics, angiotensin-converting enzyme inhibitor (ACE inhibitor) antihypertensives, central-acting adrenergic antihypertensives, diuretic antihypertensive agents, and peripheral vasodilator antihypertensives.

15. A method for treating congestive heart failure in a subject who has congestive heart failure comprising administering to the subject an effective amount of a pharmaceutical composition comprising one or more 75 kD transmembrane neurotrophin receptor (p75$^{NTR}$) antagonist peptides having the sequence selected from the group consisting of: CATDIKGAEC (SEQ ID NO: 1), ATLDALLAALRRIQ (SEQ ID NO: 8) and CFFRGGFFNHNPRYC (SEQ ID NO: 9).

16. The method of claim 15, wherein the composition comprises at least one additional cardiotropic agent.

17. The method of claim 16, wherein the cardiotropic agent is selected from the group consisting of cardiac glycosides, β-blockers, calcium channel blockers, nitrates, class I antiarrhythmics, class II antiarrhythmics, angiotensin-converting enzyme inhibitor (ACE inhibitor) antihypertensives, central-acting adrenergic antihypertensives, diuretic antihypertensive agents, and peripheral vasodilator antihypertensives.

* * * * *